(12) United States Patent
Bahmani

(10) Patent No.: US 7,958,848 B2
(45) Date of Patent: Jun. 14, 2011

(54) METHOD FOR ARTIFICIAL BREEDING OF FARMED STURGEON

(76) Inventor: Mahmoud Bahmani, Rasht (IR)

( * ) Notice: Subject to any disclaimer, the term of this patent is extended or adjusted under 35 U.S.C. 154(b) by 190 days.

(21) Appl. No.: 12/475,472

(22) Filed: May 30, 2009

(65) Prior Publication Data

US 2010/0303952 A1 Dec. 2, 2010

(51) Int. Cl.
*A01K 63/00* (2006.01)

(52) U.S. Cl. ........................................... 119/215

(58) Field of Classification Search ............... 119/215, 119/200, 216, 217, 230
See application file for complete search history.

(56) References Cited

U.S. PATENT DOCUMENTS

2009/0246335 A1* 10/2009 Koehler-Guenther ........ 426/300

FOREIGN PATENT DOCUMENTS

| CN | 101283814 A | * | 10/2008 |
| RU | 2260943 C2 | * | 9/2005 |
| SU | 719571 A | * | 3/1980 |
| SU | 1084005 | * | 4/1987 |

* cited by examiner

*Primary Examiner* — Yvonne R. Abbott
(74) *Attorney, Agent, or Firm* — Barry ChooBin; Choobin & Choobin Consultancy L.L.C.

(57) ABSTRACT

A method for artificial breeding of farmed sturgeon is disclosed. The method comprises of growing a plurality of fingerling sturgeon; obtaining a plurality of juvenile sturgeon; identifying at least one male juvenile sturgeon and at least one female juvenile sturgeon; Feeding a predetermined amount of a preselected food material to the male and female sturgeon; Determining maturity based on at least controlling sex hormones and stress hormones of the male and female sturgeon; identifying at least one male matured sturgeon and at least one female matured sturgeon; and Selecting male matured sturgeon and female matured sturgeon, wherein said female matured sturgeon carries a predetermined amount of ovule and wherein said predetermined amount of ovule is processed to obtain a predetermined amount of caviar.

7 Claims, No Drawings

METHOD FOR ARTIFICIAL BREEDING OF FARMED STURGEON

SPONSORSHIP STATEMENT

The present invention is sponsored by Iranian National Science Foundation for international filing.

BACKGROUND OF INVENTION

Sturgeons are an interesting and unique species of fish known for their economic value and biological significance. With regard to its unique physiological requirements, relatively shorter period required for sexual maturity and higher resistance to stress as compared to other species, the culture of A. stellatus has received a lot of attention in the recent years. However a long term commitment to an integrated approach to achieve the biotechnique of brood stock production can be beneficial for the development of sturgeon aquaculture.

Successful recovery of sturgeon stocks is dependent on many factors including investigations on the functioning of their reproduction system and factors responsible for the improvement and development of gonads. However the peculiarities of sturgeon gonads and their prolonged sexual maturity were obstacles while investigating trends in gonad development. Under natural conditions, female A. stellatus begin to reproduce at an age of 8 to 17 years, while the equivalent age in males is 5 to 13 years. Factors affecting reproduction and growth in fishing including sturgeons can be divided into categories; internal factors and external factors. Among the internal factors, genetic and physiological factors and all processes related to endocrine glands are considered to be important, while a wide array of ecological factors including light, temperature, pH, feeding and certain physical and chemical characteristics of water are considered as critical external factors affecting reproduction. Diet composition is one of the most important deterministic external factors that affect gonadal development in fish.

Highly unsaturated fatty acids (HUFA) with 20 or more carbon atoms affect, directly or through their metabolites, fish maturation and steroidogenesis. In some species, HUFA in broodstock diets increases fecundity, fertilization and egg quality. As in higher vertebrates, vitamin E deficiency affects reproductive performance, causing immature gonads and lower hatching rate and survival of offspring. HUFA deficiency in diets led to delay in vitellogenesis in rainbow trout (Oncorhynchus mykiss). On the other hand HUFAs also play an important role in regulating the synthesis of ecosanoids and prostaglandins, a large group of highly bioactive hormones that stimulate the production of steroids, gonad development and ovulation. Fish farmed on diets containing HUFA have been known to show increased fertilization rates and fecundity as well as increase in quality and survival of eggs and hatching rates. Apart from HUFA, vitamin C (ascorbic acid) and E ($\alpha$ tocopherol) are important because of their powerful antioxidant properties during different stages of development of reproduction system in fish.

Vitamin E is a fat soluble vitamin which acts as an antioxidant essential for reproduction in vertebrates. Deficiencies in Vitamin E leads to delay in development of gonads, decrease in hatching rates and lowering survival rate of larvae. Natural antioxidants, including vitamin E, and C play important roles in reproduction by maintaining antioxidant protection of the spermatozoa during spermatogenesis and affects their motility, membrane fluidity and fertility.

Vitamins C and E neutralizes unstable free radicals that are produced during the production of other steroid hormones. The antioxidant function of vitamins C and E can provide an important protective role for the sperm cells during spermatogenesis and until fertilization by reducing the risk of lipid peroxidation, which is detrimental for sperm motility. Ascorbic acid has been shown to play an important role in salmonid reproduction and its role in steroidogenesis and vitellogenesis has been reported. The role of vitamin E has also been documented in gonadal development and fertilization rate in carps.

The role of vitamin C in the functioning of the reproduction system in salmonidae has been studied. Vitamin C is also critical in the survival and development of larvae and it is also effective in the formation of collagen, during embryonic development.

Phytoestrogens a diverse group of naturally occurring non steroidal plant compounds found in soybean extract are known to affect vitellogenesis and advance oocyte maturation. Genistein, an estrogenic isoflavone compound on the endocrine process of gametogenesis and on reproduction efficiency of the rainbow trout Oncorhynchus mykiss has been studied. The effects of genistein and equol on the gonadal development of Japanese Medaks (Oryzia latipes) have been documented.

The gonadal structure in different sturgeon species is dependant on the different stages of growth. Therefore the stage of gametogenesis may be used as index for all sturgeon species. Several papers have demonstrated that certain blood parameters can be used as indicators of the physiological condition of the fish during the selection of brood stock. With regard to the significance of artificial breeding programs of farmed A. stellatus to develop sturgeon aquaculture in the country, the investigation of blood parameters has been considered an important aspect of this study. Hematological studies give us an insight of gonadal growth and development of these species under farmed conditions and thus can be valuable in the conservation of these valuable stocks.

Considering that sexual maturity in sturgeons is reached very late an improvement in broodstock nutrition and feeding can greatly improve egg and sperm quality.

The main objective of this study is to investigate the effects of diets containing soybean and vitamins C and E in the advancement or induction of sexual maturity in farmed A. stellatus and to develop a relationship between dietary nutrients that affect gonadal development and fecundity in this species and other factors such as sex, farming conditions, and ecological factors. To accomplish this, the relationship between blood parameters, osmosis and sex hormones in male and female farmed A. stellatus during different stages of sexual maturity and different seasons was studied and effective indices to differentiate spawners were developed. In this way the biotechnique of brood stock production and artificial breeding and rearing of farmed sturgeons, particularly A. stellatus was developed for the first time in Iran. This will no doubt revolutionize the aquaculture industry in the country.

The operating stages of this project were carried out in three phases:
1. Brood stock production through control of physical-chemical parameters in water and using different diets in both sexes (males and females)
2. Study of histological and hematological parameters and osmosis of ions and hormones
3. Artificial breeding, harvesting of eggs and sperm and caviar and offspring
4. production using GnRH protocol

DETAIL DESCRIPTION OF THE INVENTION

This study was conducted at the International Sturgeon research Institute from the summer of 2003 through the summer of 2007 on 5 and 6 year-old sturgeon (*Acipenser stellatus*) specimens. A total of 32 farmed *A. stellatus* specimens (12 male+20 female) were stocked in groups of 4 in eight fiberglass tanks (4 tons capacity) on the basis of their sexual maturity. Male fish in stage I and II of sexual maturity were fed diets without soybean and without vitamins, male fish in stage III-IV of sexual maturity were fed diets without soybean but containing soybean and vitamins. Females in stage II of sexual maturity were fed diet containing soybean, without vitamin and females in stage III of sexual maturity were fed diets containing soybean and vitamins.

The results of the study indicate that food composition (soybean and vitamins C and E) played a significant and positive role in the reproduction system of female. Significant effect of treatment ($P<0.05$) was observed in nucleus circumference, egg circumference and ratio of nucleus diameter to egg diameter in female fish fed diets containing soybean and vitamin indicating progress in their sexual maturity. However in males, temperature was seen to be more effective in controlling sexual maturity. Suitable temperature regimes in terms of active feeding need to be implemented in the case of males.

Evaluation of blood indices in the fish under study showed significant differences ($P<0.05$) in serum osmolarity during different stages of sexual maturity in the different seasons studied.

Significant differences were also detected in the concentration of ions (Na, K, Ca, and Mg) in females in stages II, III, and III-IV of sexual maturity. However decreasing trends were observed in the concentration of Ca in stage IV females during the different seasons which coincided with the progress in sexual maturity reaching a minimum in spring. Concentration of Mg showed fluctuations in different seasons in stage IV females with the progress in sexual maturity and reached a minimum in spring. Therefore these two factors may be considered as indices in determining sexual maturity in farmed *A. stellatus*.

In males, in addition to Ca and Mg, fluctuations were also observed in Na concentrations, which reached a maximum in winter in stage III males, only to decrease again in spring. Irregular fluctuations were observed in Mg concentrations during different seasons, reaching a maximum in summer and winter and decreasing in spring and autumn. Similar trends were recorded for Na and Mg ions in stage III-IV males. However unlike in females, no significant differences were observed in the concentration of Ca in stage IV males.

Variations in hormones in male spawners were quite similar to that in females. Increasing trends in testosterone levels and decreasing trends in $17\alpha$ hydroxyl progesterone coincided with embryogenesis in stage III males. Fluctuations were recorded for testosterone levels in stage IV males, which reached a minimum in spring and autumn and a maximum in summer and winter. Irregular variations were recorded in $17\alpha$ hydroxy progesterone levels in stage IV males which declined from summer to winter and increased in spring.

It is evident from the results obtained that stage IV females showed significant variations in testosterone levels which simultaneously increased with the progress in embryogenesis and reached a maximum in spring. On the other hand declining trends were recorded for $17\alpha$ hydroxy progesterone which reached a minimum in spring. Therefore these two hematological factors may be considered as suitable physiological indices in staging gonadal development and determining final maturation in farmed *A. stellatus* when selecting suitable spawners for artificial breeding.

As compared to females, testosterone and $17\alpha$ hydroxy progesterone levels in male spawners showed fluctuations during the early stages of development. Increasing trends were recorded for testosterone levels which coincided with the progress in embryogenesis and reached a maximum in spring. However declining trends were recorded for $17\alpha$ hydroxy progesterone which reached a minimum in spring. No significant differences were detected in testosterone and $17\beta$ estradiol levels recorded before injection, 12 h after injection (coinciding with the second injection) and after ovulation.

Farmed *Acipenser stellatus* breeders used for artificial breeding were injected a combination of GnRH following the two dose protocol (dose=10 µg/kg; interval=6-12 h and ratio=80:20) in females and the single dose protocol (dose=20 µg/kg) in males.

Significant differences were detected in serum osmolarity of females prior to injection, 12 h after injection (during second injection) after ovulation (24 h after injection), and in females that did not respond to injection and in serum osmolarity of males prior to injection, 6 h after injection, after spermiation (12 h after injection) and showing incomplete spermiation.

Creation of brood stock, harvesting suitable eggs and the production of farmed caviar, harvesting viable sexual products from farmed specimens, successful artificial breeding programs in farmed *A. stellatus* using the micro incision method of the ovary without sacrificing the spawner and producing offspring from farmed specimens in the years 2006 and 2007 are among the various successful achievements of the present study. This study places emphasis on applied research and commercialization of the results of this research towards the development of artificial breeding and rearing in sturgeons to produce caviar and enhance sturgeon aquaculture in the country.

Physiological Investigations to Study Drawbacks in Artificial Breeding of *A. stellatus*

A new formulation of GnRH and synthetic compound of anti-dopamine "domperidone" was used for the first time in Iran with modern methodology to determine suitable physiological indices for reproduction and to resolve the present problems of artificial reproduction in stellate sturgeon *Acipenser stellatus*. This study was conducted through three experimental phases on 172 *A. stellatus* spawners (76 male and 96 female). The first experimental phase was conducted on 25 female and 22 male spawners, the second phase was conducted on 31 female and 34 male spawners and the third phase was conducted on 60 spawners including 40 female and 20 male specimens caught at catch stations in the vicinity of the SefidRud River. Male spawners were treated using single injection method and dual injection method was used in females (Bio-physiological control).

Propylene glycole (PG) was administered after the muscular injection to increase the viscosity of the solution during absorption following intramuscular injection near the second dorsal scute. Depending on the stage of sexual maturity in the brood fish, GnRH at the dose of 5, 10, 15, 20, 30, 40, 50 and 60 µg kg$^{-1}$ was used in combination with a dose of 1 or 2 mg kg$^{-1}$ of domperidone.

The position of GV was used to determine Polarity Index (PI) of sexual maturity in females while in males sexual maturity was determined on the basis of testis quality. The brood fish under study showed GV in the range of 3.64 to 14.30.

The obtained results confirm that reduction of stress during catch, transportation, maintenance and handling and selection of spawners with suitable morphology will result in increased reproduction potential.

Analysis of data obtained indicates that male brood fish given a dose of 20 and 30 µg kg$^{-1}$ GnRH along with 1 and 2 mg kg$^{-1}$ of domperidone and female brood fish given a dose of 10, 15 and 20 µg kg$^{-1}$ GnRH along with 2 mg kg$^{-1}$ of domperidone exhibit the most suitable conditions for spermiation and ovulation and thus in turn respond well to artificial breeding provided they possess GV in the range of 3.64 to 14.30 depending on the water temperature until the germinal vesicle break down (in vivo).

The final formulation of GnRH in combination with antidopamine domperidone used in the first and second experimental phases was effective in presenting a protocol for artificial breeding in *A. stellatus* for the third phase of study. On the basis of morphometric measurements recorded in spawners, fork length varied from 117 to 144 cm with a mean of 129.02±1.09 cm, total weight varied from 7 to 15 kg with a mean of 10.53±0.3 kg, age varied from 10 to 16 y with a mean age of 12.75±0.216 y, total weight of eggs varied from 1000 to 2900 g with a mean value of 1923.08±73.8 g, number of eggs per gram eggs varied from 82 to 129 with a mean number of 96.23±1.9 eggs, fertilization percentage varied from 6 to 90% with a mean rate of 53.37±5.06%, absolute fecundity varied from 112800 to 24940 eggs with a mean value of 180384.62±5420.9 eggs, Gonado Somatic Index (GSI) varied from 14 to 25.5 with a mean value of 18.131±0.41 and HSI varied from 0.48 to 1.1 with a mean value of 0.8146±0.1. Water temperature at the time of injection varied from 16 to 21° C. with a mean value of 18.88±0.3° C.

Hormonal and biochemical indices in female *A. stellatus* spawners used for artificial breeding in the third experimental phase were also studied. The levels of 17-α hydroxy progesterone varied from 0.0 to 0.74 ng/ml with a mean value of 0.103±0.013 ng/ml, progesterone varied from 0.017 to 0.263 ng/ml with a mean value of 0.085±0.008 ng/ml, 17β estradiol varied from 0.579 to 8.31 ng/ml with a mean value 5.86±0.32 ng/ml, testosterone values ranged from 3.8 to 168 ng/ml with a mean value of 83.65±6.3 ng/ml, levels of glucose metabolites ranged from 26 to 108 mg/dl with a mean value of 51.23±2.03 mg/dl and those of calcium ranged from 3.3 to 11.66 mg/dl with a mean value of 8.45±0.25 mg/dl.

Thus on the basis of results obtained it is evident that by selecting of brood fish with suitable morphology and identifying correct stage of sexual maturity we can achieve higher production by substituting GnRH with a combination of GnRH and antagonist dopamine (domperidone). Therefore this compound can be recommended as a suitable scientific substitute for pituitary extract and other gonadotropine analogues in the artificial breeding of sturgeon (*A. stellatus*) in sturgeon hatcheries.

Material and Methods

Sturgeon (*A. stellatus*) specimens required for this study were selected which included 5 year olds and six year old that were maintained at the International Sturgeon Research Institute. The study was conducted from summer 2003 through summer 2007. The fish were stocked in groups of 4 in eight fiberglass tanks (4 tons capacity) covered with a net to prevent the fish from jumping out of the tanks, on the basis of sex and their sexual maturity. Tanks were filled with water from the Sepidrud River. A central air blower was installed in the Fish breeding and rearing department of the Institute which was used to aerate the tanks. Water temperature and dissolved oxygen concentrations in the study tanks were measured and recorded throughout the experiment. Feeds required for fish in each tank was calculated on the basis of the biomass of the fish.

All fish under study were fed four times a day (9.00 am, 13.00 pm, 19.00 pm and 24 midnight) at the rate of 2-3% of body weight (reaching 8% of body weight in summer) throughout the experiment. Four experimental trials were studied using different diets and two replicates were used for each trial (Table 1)

TABLE 1

Experimental diets used in the present study

| Diet | composition | sex | Sexual maturity stage | Group |
|---|---|---|---|---|
| A | Basic diet + soybean | Female | End of sage II | D5, E5 |
| B | Basic diet + soybean + vitamins C & E | Female | Stage III | D6, E7 |
| C | Basic diet + vitamins C & E | Male | Stage III-IV | D7, E6 |
| D | Basic diet | Male | Stage I and II | D4, E4 |

Diet Formulation

The composition of experimental diets was determined by the Fish Processing Technology Department of the Institute following standard methods (AOAC). All ingredients (fish meal, soybean extract, meat and bone powder, etc) were first ground in a grinder and then mixed together in a mixer for 20 min. Then salt, vitamin premix, mineral supplements, vitamin C and E (Vitamin C and E and soybean extract was used), choline etc. were added to the feeds and mixed well for 15 min (Table 2). At this stage vegetable and animal oils were added to the mix and again mixed for 15 min. The mix was then made into granules (depending on the mouth size of the fish) and the granules were dried in a drier for 24 h at 30° C. After drying the feeds were packed in plastic bags and labeled and stored in a freezer at −20° C. until they were used for feeding. Before feeding the fish, feeds were removed from the freezer and kept at room temperature. Feeds were weight accurately using a digital balance and then fed to the fish.

TABLE 2

Vitamin C & E content and soybean percentage in experimental diets

| Diet | composition | Soybean content | Vitamin E content | Vitamin C content |
|---|---|---|---|---|
| A | Basic diet + soybean | 10-15% substitute for fish meal | — | — |
| B | Basic diet + soybean + vitamins C & E | 10-15% substitute for fish meal | 500 mg per kg feed | 200 mg per kg feed |
| C | Basic diet + vitamins C & E | — | 500 mg per kg feed | 200 mg per kg feed |
| D | Basic diet | — | — | — |

Biometric Measurements

After collecting blood samples and preparing blood smears all fish were measured and their total weight (up to the nearest 100 g), total length (up to the nearest 0.1 cm), fork length and meristic counts including distance between pectoral fin and ventral fin (PV), distance between anal fin and fork (LX) and circumference of abdomen were measured and recorded.

Sex Determination

Gonad Sampling

A small section of the gonads of each fish was removed using a thin rod or by biopsy and gonadal staging in males and females was carried out using histological methods.

In the biopsy method the fish were first anesthetized for 5-10 min in a water bath containing 250 ppm clove powder. Then a small slit (4-5 cm) was made on the ventral side of the body corresponding to the forth bony scute. A small section of the gonad was removed and the slit was stitched and the stitch area was cleaned with betadine solution and 5% chloramphenicol. To prevent infection, the surgical area was injected with 3-4 ml of 5% tetracycline.

Laboratory Methods

Serological Examinations

Pretreatment of Blood Serum

Test tubes containing 3 cc blood samples were transferred to the Physiological and Biochemistry Department of the International Sturgeon Research Institute. To separate serum from blood cells the blood samples were centrifuged (Model Labofuge 200 Made in Heraeus Sepatech, Germany) for 5 minutes at 3000 rpm. The serum was then pipetted into eppendorf tubes (1.5 cc) labeled and stored at −20° C. until they were used (Pottinger and Carrik, 2001). Serological examinations (ions and hormones) of samples were carried out at the Dr. Fadaee Laboratory in Rasht.

Calcium and Magnesium Analysis

Calcium and magnesium content in serum samples were determined using calorimetric methods. The color intensity of the complex depended on the Ca ion content. To prevent the interaction of magnesium, 4 mmol/l of 8-hydroxyquinolin was added to the medium. Calcium and magnesium concentrations were determined using kits (Man, Iran) and spectrophotometer (Model 1000, Technicon Co., USA).

Sodium and Potassium Analysis

Sodium and potassium content was determined using flamephotometer (Model Corning 480, Jenway Co. England). The concentration was expressed in terms of milli equivalent per liter (meq/l) which in the case of sodium and potassium (single valency) is equivalent to mmole/l.

Osmolarity

Osmolarity was determined using an automatic osmometer (Model Type-13, Nr. 9610003, Rebling Co., Germany). 1.5 cc of serum was transferred to eppendorf tubes using microsampler (Model Eppendorf, Germany). The osmometer is calibrated against distil water and standard salt solutions. The osmolarity of blood serum is expressed in terms of mosmol/l.

Protein Content in Blood Serum

Protein in blood serum was determined using a refractometer (Model SPR-Ne, Japan). To do this a drop of serum is placed on the optical surface of the refractometer. A lid is lowered over the sample. The person looks through an eyepiece and reads the value from a scale etched on the lens. The round optical field is split with dark above and light below at the point on the scale corresponding with the grams of total protein per 100 ml of blood (g/100 ml).

Determination of Serum Glucose

Glucose reagent is used to determine glucose concentration in serum by a timed endpoint method using RA-1000 system.

Hormone Indices in Blood Serum a) Testosterone Determination

Testosterone levels were determined using kits manufactured by Immunotech Co., France and the tracer I125 using Radioimmunoassay (RIA) technique using a LKB gamma counter and was expressed in terms of ng/ml.

a) Progesterone

The quantitative determination of progesterone is done using BIOSOURCE kits and 125 I detector using Radioimmunoassay (RIA) technique using a LKB gamma counter c) Determination of 17-α Hydroxy Progesterone and 17-β Estradiol The levels of these hormones were determined using kits manufactured by Immunotech Co., France and the tracer I125 using Radioimmunoassay (RIA) technique using a LKB gamma counter and was expressed in terms of ng/ml.

b) Cortisol

Cortisol was determined using Diasorin kits and 125 I detector using Radioimmunoassay (RIA) technique using a LKB gamma counter.

Cytological Examination

Blood Smears and Staining

Blood smears were prepared following the procedure given below:

Immediately after sampling, blood place a small drop of blood on clean slides

1. Fix slides in methanol 5-7 minutes.
3. Air dry.
4. Dilute Giemsa Stain 1:10 with deionized water. Color can be varied by diluting in buffer.
5. Stain film for 15-60 minutes.
6. Rinse in deionized water.
7. Air dry and evaluate Leucocyte Count Leucocyte count was determined using a light microscope (Nikon E600, Japan) using the zigzag counting method. Three slides were prepared from each blood sample and 100 fields were counted in each slide.

Hematocrit Test

Hematocrit is the proportion of blood volume that is occupied by red blood cells and is determined in two ways in laboratories:

1. After sampling and before clotting Draw the specimen into an appropriate capillary tube. Fill in the tube to about ¾ length.
2. Seal both the ends of the tube with soft wax or modelling clay. It is plugged to a depth of about 1 centimeter
3. Place the capillary tubes in a hematocrit centrifuge (Model D-78532 Tuttlingen, Hettich Co., Germany.
4. Close the centrifuge cover and centrifuge the tubes at high speed (about 7000 RPM) for 5 minutes.
5. Remove the capillary tube. It will show three layers—(a) Clear plasma at the top, (b) Whitish buffy coat at the middle and (c) column of red cells at the bottom.
6. Hold the tube against the hematocrit scale so that the bottom of the column of red cells is aligned with the horizontal zero line (exclude the height of clay).
7. Move the tube across the scale until the line marked 1.0 passes through the top of the plasma column.
8. The line that passes through the top or the column of red cells gives the value of PCV (hematocrit).

Blood Sedimentation (Westergren Method)

This is a simple and widely used method and has been declared as a standard method to measure the erythrocyte sedimentation rate.

To perform the test, anticoagulated blood is placed in an upright tube, known as a Westergren tube and the rate at which the red blood cells fall is measured and reported in mm/h. Westergren-type glass pipets of 300-mm length mounted vertically in a Westergren rack or stand. Westergren pipettes, both glass and plastic, have an internal diameter which is less than 2.55 mm. and calibrated from zero to 200 ml. The capacity of these pipettes is about 1 ml.

Diluents for Blood Cell Counting

Diluents permit the counting of white blood cells, red blood cells and platelets. This solution should be prepared fresh with the following composition:

1 ml of 2% Sodium citrate
2 ml of 1% gentian violet
1 ml of 0.1% brilliant crysel blue in ringer solution
Mix the three solutions and filter Counting Chambers Counting chambers used for counting white blood cells, red blood cells and platelets are called hematocytometer. These chambers are used for manual counting of blood cells. The most common type of hematocytometers are made of thick glass with double counting chambers.

GnRH Injection

All female spawners were injected GnRH at a dose of 10 µg/kg body weight in two stages at 6 h intervals. Males are injected a single dose of 20 µg/kg body weight which coincides with the second dose of females.

Confinement and Feeding of Spawners after Ovulation (Egg Removal) and Spermiation (Milting)

Feeding of spawners (male and female) began 24 h after removal of gametes and artificial breeding. Spawners were transferred to concrete tanks and then to fiber glass tanks for prolonged confinement and were fed after 24 h. To prevent any type of infection spawners were given daily injections of 2 cc of oxyvet antibiotic for a period of one week.

Dopamine Antagonists

The effects of different groups of dopamine antagonists administered with or without LHRH-A was first studied in goldfish of which only two hormone based compounds pimozide and domperidone particularly the latter was recommended as a suitable scientific substitute for pituitary extract and other gonadotroine analogues in the artificial breeding of *A. stellatus* in sturgeon hatcheries.

Pharmacology and Formulation of Domperidone

Domperidone injected at a rate of 1-5 mg/kg body weight in combination with pituitary gland induced spawning and gonadal development in goldfish. Although lower doses of domperidone were effective in increasing GtH levels, but spawning was not induced. Domperidone has a stimulating effect on GnRH. It is injected in a 0.1% suspension in physiological serum (0.7% salt and 0.1% sodium meta bisulfate). Domperidone is commercially used in combination with GnRH to induce spawning in fish.

Domperidone is usually used as a fast water dispersable tablet which is used for human (Motilium-Janssen). This drug is incorporated in dimethylsulphoxide (DMSO) at a rate of 0.2 ml in each tablet and in suspension in 0.5 ml propylene glycol (PG).

Linpe Method

The technique—called the Linpe method—induces ovulation in female fish by injecting them with a combination of a synthetic gonadotropin-releasing hormone analogue (LHRN-A) and the drug domperidone. It was introduced by two scientists Lin and Peter and has been very effective in carps. Although carp pituitary or HCG has been used in artificial breeding of carps, Linpe method has showing higher potency and being more stable during storage has replaced the traditional fish spawning methods in recent years. The antagonist roles of dopamine (domperidone, pimozide and rezrepine) have been studied in some bony fish species. Sturgeon are a group of polycyclic species which spawn more than one time during their life.

Artificial Breeding Performance in Farmed *A. stellatus* Spawners

*A. stellatus* spawners on transfer to the Kurenski ponds at the Shahid Beheshti hatchery and to Swedish tanks at the International Sturgeon Research Institute were divided into different experimental groups and selected for artificial breeding.

Administration of Combination Hormones

Gonadotropin releasing hormone, GnRH is used to induce final maturation in *A. stellatus* spawners. Spawners are given an intramuscular injection, below the second dorsal scute.

Protocol for GnRH Administration in Spawners

A) The first experimental phase was conducted on 25 female and 19 male *A. stellatus* spawners. The Primary GnRH product was used to test the potency of the product and to develop a protocol for its application in the artificial breeding of spawners. The doses (10:90, 30:70, 50:50) were given in one, two and three stages using 30, 50 and 60 µg/kg body weight GnRH.

B) Based on the physiological indices observed using primary GnRH in the first phase, the second phase of the project used three types (A, B, C) of GnRH in combination with an organic polymer and domperidone as the most suitable dopamine antagonist. By altering the type C synthetic GnRH, the potency of this product to induce spawning was investigated in 31 female and 34 male *A. stellatus* spawners.

In this phase female spawners were injected a GnRH dose of 5-20 µg/kg body weight, while male spawners were injected a dose of 10-20 µg/kg body weight GnRH in one or two stages in combination with 5-10 mg/kg domperidone.

C) In the final phase, propylene glycole (PG) was administered after the intramuscular injection of GnRH to increase the viscosity of the solution during absorption. GnRH at a rate of 10, 15, 20 and 30 µg kg$^{-1}$ was used in combination with a dose of 1 or 2 mg kg$^{-1}$ of domperidone on 25 female (15 used as control) and 12 male *A. stellatus* spawners (8 spawners used as control).

Developmental Stages of Ovary after Injection

Direct in vivo method was used to study the effects and physiological adaptation of GnRH on oogenesis in ovaries. In this method a small incision was made ventro-lateral part of the body and oocyte samples were collected at 1, 3, 6, 9 and 12 hours after GnRH injection. About 5-10 eggs were sampled that were immediately sectioned and examined under the microscope at the Physiology and Biochemistry department of the Institute.

Artificial breeding of *A. stellatus* Spawners.

After inducing ovulation in female and spermiation in male spawners, artificial breeding of spawners was carried out in the Shahid Beheshti hatchery and International Sturgeon Research Institute following the guidelines of the biotechnique developed from the present study.

Statistical Methods

Descriptive statistics was used to calculate minimum, maximum, standard deviation, variance and standard error of means of the data obtained for blood parameters (serological and cytological) and morphological parameters. One way and two way analysis of variance and Tukey test was used to determine significant differences between trials at 95% confidence level using computer based software such as Excel and SPSS.

TABLE 3

Biometric indices in female fish

| Group | Diet | Mean weight (kg) in different seasons | | | | | Mean length (cm) in different seasons | | | | |
|---|---|---|---|---|---|---|---|---|---|---|---|
| | | Summer | Autumn | Winter | Spring | Summer | summer | Autumn | Winter | Spring | Summer |
| D5 | With soybean without vitamin | 0.04 ± 2.32 | 0.29 ± 2.8 | 0.32 ± 3.2 | 0.24 ± 3.8 | 0.19 ± 4.2 | 4.8 ± 86.11 | 3.8 ± 88.7 | 2.8 ± 92.32 | 3.7 ± 95.4 | 1.67 ± 97.66 |
| E5 | With soybean without vitamin | 0.57 ± 4.02 | 3.7 ± 4.6 | 0.42 ± 5.1 | 0.52 ± 5.6 | 0.61 ± 5.6 | 4.7 ± 99.61 | 1.5 ± 101.5 | 2.4 ± 104.1 | 3.9 ± 105.2 | 2.8 ± 106.2 |
| D6 | With soybean with vitamin | 0.47 ± 3.8 | 0.36 ± 4.1 | 0.28 ± 4.5 | 0.49 ± 4.8 | 0.39 ± 5.1 | 3.4 ± 91 | 2.8 ± 94.3 | 1.4 ± 96.7 | 4.5 ± 99.6 | 6.22 ± 101.5 |
| E7 | With soybean with vitamin | 0.75 ± 3.8 | 0.45 ± 4.4 | 0.65 ± 4.6 | 0.78 ± 4.8 | 0.78 ± 4.8 | 2.3 ± 86.8 | 4.2 ± 89.4 | 2.6 ± 94.5 | 3.8 ± 97.6 | 4.9 ± 99.2 |

Trial A (with Soybean without Vitamin)

Group D5 includes female specimens fed diets containing soybean and without vitamin. Fish in this group were in late stage II of sexual maturity at the beginning of the experiment and in stage III of sexual maturity at the end of the experimental period. Variations in biometric measurements conducted were as follows:

Significant differences (P<0.05) were observed in fork length (cm). Highest fork length observed in summer of 2004 was 97.66±1.67, while lowest fork length in summer of 2003 was 86.11b±4.81.

Significant differences (P<0.05) were also observed in variations in total length (T1) of spawners. Highest T1 (105.84a±1.08) were recorded in summer of 2004 and lowest T1 (96.53b±3.12) were recorded in summer of 2003.

Significant differences (P<0.05) were also recorded in total weight of spawners in the different seasons studied. Highest weight (4.2a±0.19) were recorded in the summer of 2004 while lowest weight (2.32b±0.04) of spawners were recorded in the summer of 2003.

Male *Acipenser stellatus* Spawners

TABLE 4

Biometric indices in male spawners

| Group | Diet | Mean weight (kg) in different seasons | | | | | Mean length (cm) in different seasons | | | | |
|---|---|---|---|---|---|---|---|---|---|---|---|
| | | Summer | Autumn | Winter | Spring | Summer | summer | Autumn | Winter | Spring | Summer |
| D7 | With soybean without vitamin | 0.28 ± 2.45 | 0.34 ± 2.78 | 0.54 ± 2.94 | 0.64 ± 3.1 | 0.78 ± 3.3 | 4.9 ± 86.5 | 2.3 ± 87 | 1.5 ± 88 | 2.5 ± 89 | 3.7 ± 91.5 |
| E6 | With soybean without vitamin | 0.34 ± 4.02 | 0.27 ± 3.1 | 0.16 ± 2.9 | 0.27 ± 3.1 | 0.38 ± 3.2 | 3.2 ± 83.4 | 4.9 ± 84 | 2.3 ± 85 | 3.7 ± 87 | 2.5 ± 88.2 |
| D4 | With soybean with vitamin | 0.6 ± 6.0 | 1.3 ± 7.5 | 1.2 ± 7.2 | 1.3 ± 7.5 | 1.5 ± 7.9 | 2.5 ± 95.3 | 3.7 ± 98.4 | 2.7 ± 104.7 | 3.7 ± 107.6 | 4.5 ± 109.5 |

TABLE 4-continued

Biometric indices in male spawners

| | | Mean weight (kg) in different seasons | | | | | Mean length (cm) in different seasons | | | | |
|---|---|---|---|---|---|---|---|---|---|---|---|
| Group | Diet | Summer | Autumn | Winter | Spring | Summer | summer | Autumn | Winter | Spring | Summer |
| E4 | With soy-bean with vita-min | 1.6 ± 4.1 | 1.4 ± 5.2 | 2.1 ± 4.8 | 1.4 ± 5.2 | 1.5 ± 5.4 | 1.7 ± 90.4 | 4.2 ± 94 | 5.4 ± 96 | 6.5 ± 98 | 3.4 ± 100.2 |

Trial C (without Soybean with Vitamin)
Group D7 includes male spawners fed diets without soybean but with vitamin. Fish in this experimental group were in stage II of sexual maturity in the beginning of the experiment and in stage III-IV of sexual maturity at the end of the experimental period.
No significant differences ($P \geq 0.05$) were observed in fork length (cm). Highest fork length observed in summer of 2004 was 91.5a±3.77, while lowest fork length in summer of 2003 was 86.5a±4.09.
No significant differences ($P \geq 0.05$) were also observed in variations in total length (T1) of spawners. Highest T1 (99.8a±4.71) were recorded in summer of 2004 and lowest T1 (97.25a±5.5) were recorded in autumn of 2003.

No significant differences ($P \geq 0.05$) were also recorded in total weight of spawners in the different seasons studied. Highest weight (3.3a±0.78) were recorded in the summer of 2004 while lowest weight (2.9a±0.7) of spawners were recorded in the autumn of 2003.

Outstanding Achievements and Conclusions
a) Milt Harvest from Farmed Male *A. stellatus*
Hormone administration using GnRH with a combination of GnRH and anti dopamine (domperidone) was carried out on spawners ranging in weight from 3-6 kg and in length from 100-123 cm (Table 47). The total volume of spermatozoa harvested was 50-200 ml and the spermatocrit was 5-13% in the temperature range of 18-24.4° C.

TABLE 5

Range of variations in hormonal and biochemical indices in male farmed *A. stellatus*

| | Testosterone (ng/ml) | 17-α hydroxy progesterone | Hematocrit (%) | Osmolarity (mosmol/l) |
|---|---|---|---|---|
| Before injection | 250-410 | 0.003-0.037 | 27-34 | 222-239 |
| After milting | 198-600 | 0.025-0.17 | 23-32 | 245-219 |

Harvesting Eggs from Farmed Female *A. stellatus*

Depending on the stage of sexual maturity in the brood fish and using GV to determine polarity index, GnRH was used in combination with domperidone to inject spawners in the weight range of 7.5-11.5 kg and in the length range of 123-133 cm (Table 48). The total eggs harvested weighed 1150-1500 g and number of eggs per gram eggs was 85-95 egg. Fertilization rate ranged from 50-87% in the temperature range of 19-24.4° C. GV values in farmed female spawners ranged from 14.7-30.

TABLE 6

Range of variations in hormonal and biochemical indices in female farmed *A. stellatus*

| | Testosterone (ng/ml) | 17-β estradiol (ng/ml) | 17-α hydroxy progesterone (ng/ml)) | Hematocrit (%) | Osmolarity (mosmol/l) |
|---|---|---|---|---|---|
| Before injection | 2.2-520 | 1.09-6 | 0.004-0.178 | 20-33 | 226-258 |
| 12 hours after first injection synchronous with second injection | 4.7-590 | 0.95-5.7 | 0.031-0.419 | 21-34 | 218-222 |
| After ovulation | 2.2-347 | 1-2.1 | 0.03-0.197 | 13-36.5 | 223-244 |

Harvesting of Eggs
Control and regulating sexual maturity in eggs was carried out by direct in vivo method and maturity of eggs and polarity index (PI) in 5 farmed female sturgeon (*A. stellatus*) spawners was carried out in 2006 and in 8 farmed female *A. stellatus* spawners in 2007 by making a micro incision at the urogenital region. This was done in open air which acts as an anesthetic, achievements of this method used and approved in other 4 species of commercial sturgeon including Beluga, *Huso huso*, Ship sturgeon, *Acipenser nudiventris* (brackish water species), Sterlet, *Acipenser ruthenus* and Siberian sturgeon, *Acipenser baerii* (fresh water species) under this examination.
b) Hormonal Tests in Male Spawners
Testosterone levels in male spawners measured prior to pituitary injection and immediately after and again 2 months after harvesting of sperms was 330, 398 and 7.9 ng/ml, respectively. The level of 17β estradiol increased after harvesting of sperms and the mean levels at the time of pituitary injection, immediately after harvesting of sperm and again 2 months after harvesting of sperms was 1.29, 1.02 and 15 ng/ml, respectively. Levels of 17α hydroxy progesterone increased after harvesting of sperm and mean levels at the time of pituitary injection, immediately after harvesting of sperm and again 2 months after harvesting of sperms was 0.02, 0.01 and 0.022 ng/ml, respectively c) Hormonal Tests in Female Spawners Testosterone levels in female spawners dropped after ovulation and mean levels at the time of pituitary injection, immediately after ovulation and again 2 months after ovulation were 261.1, 174 and 7.52 ng/ml, respectively.

Levels of 17β estradiol increased after ovulation. Mean levels of this hormone at the time of pituitary injection, immediately after ovulation and again 2 months after ovulation were 0.091, 0.113 and 0.5 ng/ml, respectively. After production of brood stock sexual maturity and other parameters in 32 farmed *A. stellatus* brood fish were measured. Nine female spawners weighing 5-9 kg were in stage IV of sexual maturity and their GV ranged from 9-24. Testosterone levels in these spawners ranged from 200-450 ng/ml. Among the farmed male spawners, sperm was harvested from 8 spawners weighing between 3-6 kg selected on the basis of their testosterone levels (315-450 ng/ml). Spawners were then injected GnRH. GV of spawners at the time of breeding ranged from 9.5-15. All female spawners were injected GnRH at a dose of 10 μg/kg body weight in two stages at 6 h intervals. Males are injected a single dose of 20 μg/kg body weight which coincides with the second dose of females. Eggs were harvested using micro incision from all female spawners except one spawner which died due to severe bleeding. Fertilization rate was between 41-95% and total weight of larvae produced was 2505 g. All male spawners responded to pituitary injection and 1500 ml sperm was harvested of which about 200 ml was stored in liquid nitrogen at −196° C. Harvesting more than 3 liter sperm was possible but due to limitations in freezing facilities, excess sperm was not harvested from the spawners.

Physiological indices of farmed *A. stellatus* spawners (females and males) are presented in tables 6 and 7.

tion cycles. Therefore mass investments made to address brood stock production of farmed sturgeons should be designed to make it possible to harvest eggs from these spawners several times during their production cycle.

After surgery, spawners are transferred to concrete tanks and maintained under suitable conditions until feeding is resumed. The micro incision method to harvest eggs from sturgeons was introduced for the first time by Padoshka (1986) in Russia and proved to be more efficient than the traditionally used method of sacrificing spawners as well as the method to harvest eggs by cesarean section of the abdomen. This method was previously attempted on wild *A. persicus* spawners in the Shahid Beheshti hatchery and in the Shahid Marjani hatchery, but all spawners died after surgery as they were not able to adapt to conditions in the hatchery.

With regard to this, the development of this technique in the country to harvest eggs from spawners several times is indispensable and appears to be a promising prospective for sturgeon spawners particularly in the recent years when their stocks are seriously threatened and/or have become extinct (particularly the autumn race). Fortunately this technique has been successfully conducted in female *A. stellatus* spawners and also shows a bright perspective for its extensive application in Iran. The advantage of this technique is that the female spawners are not sacrificed during egg harvest and it can be repeated over many production cycles for artificial breeding programs and/or for caviar production. Also owing to certain genetic characteristics and physiological anomalies overripping of eggs is observed in spawners which in captivity leads to the death of spawners. By applying this technique all the eggs are removed from the ovary and thus prevent the infection of ovary and death of the spawners.

Fertilization rate recorded using this technique was 50-85% (mean=74%). Incubation period for fertilized eggs in Yoshchenko incubators depending on water temperature took an average time of 7 days. After hatching, larvae with yolk sac

TABLE 7

Physiological indices in farmed male *A. stellatus* spawners

| Spawner No. | Weight (kg) | Testosterone (ng/ml) | Temperature (° C.) at time of injection | Response time | Sperm amount | Sperm motility | Sperm concentration | Remarks |
|---|---|---|---|---|---|---|---|---|
| 1 | 5.4 | 450 | 17.5 | 6 | 300 | Very suitable | Very concentrated | Used for artificial breeding |
| 2 | 5.1 | 430 | 17.5 | 14 | 200 | Medium | Dilute | Not used |
| 3 | 4.2 | 315 | 19.5 | 14 | 100 | Medium | Concentrated | Not used |
| 4 | 4 | 420 | 19.5 | 9 | 200 | Very suitable | Very concentrated | Cryopreservation |
| 5 | 3 | 360 | 19.5 | 14 | 100 | Suitable | Concentrated | Used for artificial breeding |
| 6 | 6.6 | 370 | 22 | 13 | 350 | suitable | Dilute | Not used |
| 7 | 4.8 | 360 | 22 | 13 | 250 | Very suitable | concentrated | Used for artificial breeding |

Despite the severe decline in sturgeon stocks, all spawners (female) caught from the wild were sacrificed for artificial breeding programs in sturgeon hatcheries (5 centers in the Gilan, Mazandaran and Golestan Provinces). Spawners from which eggs were harvested by micro incision method also died after surgery. Sturgeons are known to have long life spans (100 y in some species) and are thus capable of spawning several times during their life. Harvesting of eggs is harmless for the fish and, thus can be repeated over many producwere transferred to vniro tanks. Exogenous feeding of larvae was commenced using live food (artemia and daphnia) and continued until the larvae reached 550 mg. At present the first group of *A. stellatus* fingerlings produced from farmed spawners are being reared on formulated diets.

Brood stock production and artificial breeding of farmed sturgeons has no history in Iran. At present very few countries in Europe and America have succeeded in producing tens of tons of farmed caviar every year. With regard to the long history of Iran in sturgeon catch as well as in artificial breeding and restocking programs for sturgeons, it appears that we have not reached the attained the real status regarding production of farmed caviar and artificial breeding of farmed sturgeons. Moreover although beluga sturgeon has been introduced as a suitable candidate for sturgeon farming, with regard to the shorter age of sexual maturity, physiological adaptations and good quality of farmed spawners of *A. stellatus*, this species has been considered a more suitable candidate for sturgeon farming. Processed farmed caviar has been graded "superior".

In farmed caviar protein was between 28.3-29.1%, lipid ranged from 13.6-14.8% and humidity ranged from 47.1-52.3% (Table 50). The results obtained indicate a promising future for aquaculturists to produce farmed caviar which can be compared to caviar harvested from the wild.

TABLE 8

Comparison of chemical parameters between farmed caviar and caviar harvested from wild spawners

|  | Protein (%) | Lipid (%) | Humidity (%) |
| --- | --- | --- | --- |
| Farmed caviar | 28.3 | 14.8 | 52.3 |
| Caviar from wild specimens | 30.3 | 15.7 | 52 | d) Larval and Fingerling Rearing in *A. stellatus*

On hatching the larvae produced were weighed and transferred to double walled concrete vniro tanks. After yolk sac absorption which depending on water temperature lasted for 7-10 days, larvae were fed live food which consisted of nauplius of artemia in the early stages growth and development and then daphnia after which they were weaned to formulated diets.

CONCLUSION

The use of a new formulation of GnRH and synthetic compound of anti-dopamine domperidone with modern methodology was successful in determining suitable physiological indexes for reproduction and resolving the present problems of artificial reproduction in stellate sturgeon *Acipenser stellatus*.

Based on the protocols developed for the use of different doses under different conditions it is evident that by selecting of brood fish with suitable morphology and identifying correct stage of sexual maturity we can achieve higher production by substituting GnRH with a combination of GnRH and antagonist dopamine (domperidone) at a dose of 10 and 20 μg/kg body weight GnRH in females and a dose of 30 μg/kg body weight GnRH in males.

The results of the present study document the effectiveness of reproduction physiology of spawners, GV percentage and water temperature considered for artificial breeding of *A. stellatus* spawners in the new protocol in improving artificial breeding in these fish. This protocol can therefore be proposed as a suitable scientific substitute for the traditional methods using pituitary extract or for other gonadotropin analogues used in artificial breeding programs in sturgeon hatcheries in Iran.

The invention has been described in connection with its preferred embodiments. However, it is not limited thereto. Changes, variations and modifications to the basic design may be made without departing from the inventive concepts in this invention. In addition, these changes, variations and modifications would be obvious to those skilled in the art having the benefit of the foregoing teachings. All such changes, variations and modifications are intended to be within the scope of the invention which is limited only by the following claims.

I claim:

1. A method for artificial breeding of farmed sturgeon wherein said method comprises of:
    growing a plurality of fingerling sturgeon;
    obtaining a plurality of juvenile sturgeon, wherein said plurality of juvenile sturgeon comprises of at least one male juvenile sturgeon and at least one female juvenile sturgeon;
    identifying said of at least one male juvenile sturgeon and said at least one female juvenile sturgeon;
    Separating said at least one male juvenile sturgeon and said at least one female juvenile sturgeon;
    Feeding a predetermined amount of a preselected food material to said at least one male juvenile sturgeon and said at least one female juvenile sturgeon wherein said food material for said at least one male juvenile sturgeon consists of said predetermined amount of said preselected food material and said food material for said at least one female juvenile sturgeon consists of said predetermined amount of said preselected food material and a predetermined amount of soya;
    Determining maturity of said at least one male juvenile sturgeon and said at least one female juvenile sturgeon based on at least controlling sex hormones and stress hormones of said at least one male juvenile sturgeon and said at least one female juvenile sturgeon;
    Identifying at least one male matured sturgeon and at least one female matured sturgeon; and
    Selecting said at least one male matured sturgeon and at least one female matured sturgeon, wherein said female matured sturgeon carries a predetermined amount of ovule and wherein said predetermined amount of ovule is processed to obtain a predetermined amount of caviar.

2. The method as claimed in claim 1, wherein said method further comprises:
    Injecting a predetermined amount of treatment wherein said treatment consists of a predetermined amount of GnRH and a predetermined amount of anti-dopamine and wherein said anti-dopamine is domperidone.

3. The method as claimed in claim 2, wherein said predetermined amount of treatment for said male matured sturgeon comprises of 20 to 30 μg GnRH per kg of body weight of said male matured sturgeon along with 1 mg of domperidone per kg of body weight of said male matured sturgeon.

4. The method as claimed in claim 2, wherein said predetermined amount of treatment for said female matured sturgeon comprises of 10 to 20 μg GnRH per kg of body weight of said female matured sturgeon along with 2 mg of domperidone per kg of body weight of said female matured sturgeon.

5. The method as claimed in claim 2, wherein said injecting is performed in one stage for male matured sturgeon.

6. The method as claimed in claim 2, wherein said injecting is performed in two stages for female matured sturgeon.

7. The method as claimed in claim 6, wherein said method further comprises: ovulating said predetermined amount of ovule from said female matured sturgeon by oviduct micro incision, wherein said female matured sturgeon remains alive.

\* \* \* \* \*